United States Patent
Hopkinson

(10) Patent No.: US 11,350,945 B2
(45) Date of Patent: Jun. 7, 2022

(54) STAGED DEFLATION SYRINGE SYSTEMS AND ASSOCIATED METHODS

(71) Applicant: Merit Medical Systems, Inc., South Jordan, UT (US)

(72) Inventor: Aaron Hopkinson, Herriman, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 189 days.

(21) Appl. No.: 16/186,014

(22) Filed: Nov. 9, 2018

(65) Prior Publication Data

US 2019/0142433 A1    May 16, 2019

Related U.S. Application Data

(60) Provisional application No. 62/585,234, filed on Nov. 13, 2017.

(51) Int. Cl.
*A61B 17/12* (2006.01)

(52) U.S. Cl.
CPC .. *A61B 17/12136* (2013.01); *A61B 17/12109* (2013.01); *A61B 2017/12004* (2013.01)

(58) Field of Classification Search
CPC .............. A61M 5/3129; A61M 5/3134; A61M 5/3135; A61M 5/315; A61M 5/31501; A61M 5/31505; A61M 25/1018; A61M 25/10182; A61M 2005/3131; A61M 2005/31506; A61M 2005/31508; A61M 2005/3151; A61M 2205/073; A61M 5/178; A61M 5/31; A61B 17/12136; A61B 17/12109; A61B 17/8825; A61B 2017/12004
See application file for complete search history.

(56) References Cited

U.S. PATENT DOCUMENTS

| 1,393,720 | A |   | 10/1921 | Lomas et al. |
| 3,831,603 | A |   | 8/1974  | Armenti |
| 3,901,413 | A |   | 8/1975  | Harris, Sr. |
| 3,938,505 | A |   | 2/1976  | Jamshidi |
| 4,275,729 | A |   | 6/1981  | Silver et al. |
| 4,386,606 | A |   | 6/1983  | Tretinyak et al. |
| 4,476,866 | A | * | 10/1984 | Chin ............... A61M 25/10182 604/271 |
| 4,562,844 | A |   | 1/1986  | Carpenter et al. |

(Continued)

FOREIGN PATENT DOCUMENTS

DE    102013104018    10/2014
EP       0208975 A3    5/1987

(Continued)

OTHER PUBLICATIONS

European Search Report dated Sep. 19, 2016 for EP14771008.1.

(Continued)

*Primary Examiner* — Melanie R Tyson

(74) *Attorney, Agent, or Firm* — Dorsey & Whitney LLP

(57) ABSTRACT

Devices used to deflate an inflatable hemostasis device are disclosed. The devices may be configured to deflate the inflatable hemostasis device in staged increments over a period of time. The devices may include a barrel member and a plunger member comprising an insert configured to couple with a retention ring of the barrel to restrict a retraction distance of the plunger member.

10 Claims, 6 Drawing Sheets

(56) References Cited

U.S. PATENT DOCUMENTS

| | | |
|---|---|---|
| 4,592,746 A | 6/1986 | Burkholder |
| 4,635,792 A | 1/1987 | Yamada et al. |
| 4,711,637 A | 12/1987 | Leigh et al. |
| 4,747,484 A | 5/1988 | Ackeret |
| 4,758,232 A | 11/1988 | Chak |
| 4,807,749 A | 2/1989 | Ackeret |
| 4,810,249 A | 3/1989 | Haber et al. |
| 4,875,578 A | 10/1989 | Nehl |
| 4,929,238 A | 5/1990 | Baum |
| 4,966,581 A | 10/1990 | Landau |
| 5,000,735 A | 3/1991 | Whelan |
| 5,009,646 A | 4/1991 | Sudo |
| 5,011,010 A | 4/1991 | Francis et al. |
| 5,049,135 A | 9/1991 | David |
| 5,135,111 A | 8/1992 | Stoger |
| 5,205,823 A | 4/1993 | Zdeb |
| 5,213,209 A | 5/1993 | Son |
| 5,306,248 A | 4/1994 | Barrington |
| 5,306,258 A | 4/1994 | De La Fuente |
| 5,314,416 A | 5/1994 | Lewis |
| 5,358,497 A | 10/1994 | Dorsey |
| 5,397,313 A | 3/1995 | Gross |
| 5,411,488 A | 5/1995 | Pagay et al. |
| 5,413,115 A | 5/1995 | Baldwin |
| 5,685,864 A | 11/1997 | Shanley et al. |
| 5,735,825 A | 4/1998 | Stevens et al. |
| 5,814,917 A | 9/1998 | Isobe et al. |
| 6,203,521 B1 | 3/2001 | Menne |
| 6,234,996 B1 | 5/2001 | Bagaoisan et al. |
| 6,579,269 B1 * | 6/2003 | Kleyman .......... A61M 5/31555 604/207 |
| 7,022,112 B2 | 4/2006 | Pokorney |
| 7,604,618 B2 | 10/2009 | Dixon |
| 7,927,315 B2 | 4/2011 | Sudo et al. |
| 8,475,415 B2 | 7/2013 | Schiller |
| 9,332,972 B2 | 5/2016 | Boutaghou |
| 2002/0198500 A1 | 12/2002 | Leung |
| 2004/0138612 A1 | 7/2004 | Shermer et al. |
| 2004/0236283 A1 | 11/2004 | Tang |
| 2005/0137533 A1 | 6/2005 | Sudo et al. |
| 2006/0178643 A1 | 8/2006 | Sudo et al. |
| 2006/0195063 A1 | 8/2006 | Lim et al. |
| 2006/0264837 A1 | 11/2006 | Bloom et al. |
| 2007/0219508 A1 | 9/2007 | Bisegna |
| 2009/0247961 A1 | 10/2009 | Carlyon |
| 2009/0326479 A1 * | 12/2009 | Janish ................ A61M 5/3158 604/218 |
| 2010/0168662 A1 | 7/2010 | Bingham |
| 2010/0211000 A1 | 8/2010 | Killion et al. |
| 2011/0009829 A1 | 1/2011 | Kosinski et al. |
| 2011/0178475 A1 | 7/2011 | Tanaka et al. |
| 2011/0319864 A1 | 12/2011 | Beller et al. |
| 2012/0136298 A1 | 5/2012 | Bendix et al. |
| 2013/0123693 A1 | 5/2013 | Lampropoulos et al. |
| 2014/0031764 A1 | 1/2014 | Kabushiki |
| 2014/0052078 A1 | 2/2014 | Heinz |
| 2014/0062036 A1 | 3/2014 | Maeda et al. |
| 2014/0100509 A1 | 4/2014 | Defonzo |
| 2014/0124542 A1 | 5/2014 | Kojima et al. |
| 2014/0288408 A1 | 9/2014 | Deutsch |
| 2015/0018800 A1 | 1/2015 | Reb et al. |
| 2015/0314074 A1 * | 11/2015 | Howlett ................ A61M 39/24 604/508 |
| 2015/0320937 A1 | 11/2015 | Kosinski et al. |
| 2016/0058988 A1 | 3/2016 | Kesten et al. |
| 2016/0101269 A1 | 4/2016 | Benz |
| 2016/0243305 A1 | 8/2016 | Nakamura |
| 2016/0279395 A1 | 9/2016 | Lampropoulos et al. |
| 2017/0000988 A1 | 1/2017 | Stevens et al. |
| 2017/0007807 A1 | 1/2017 | Weerakoon et al. |
| 2017/0312177 A1 | 11/2017 | Bhargava et al. |

FOREIGN PATENT DOCUMENTS

| | | |
|---|---|---|
| EP | 0338671 | 10/1989 |
| EP | 0375778 | 7/1990 |
| EP | 0420126 | 9/1990 |
| EP | 1602389 | 12/2005 |
| JP | 02152463 | 6/1990 |
| JP | 0698921 | 4/1994 |
| WO | 199409838 | 5/1994 |
| WO | 199530444 | 11/1995 |
| WO | 199744077 | 11/1997 |
| WO | 200041494 | 7/2000 |
| WO | 2004044464 | 5/2004 |
| WO | 2007006030 | 1/2007 |
| WO | 2011006086 | 1/2011 |
| WO | 2011006103 | 1/2011 |
| WO | 2014077670 | 5/2014 |

OTHER PUBLICATIONS

International Preliminary Report dated Sep. 24, 2015 for PCT/US2014/027649.
International Search Report and Written Opinion dated May 22, 2017 for PCT/US2017/014043.
International Search Report and Written Opinion dated Oct. 20, 2016 for PCT/US2016/041047.
Office Action dated Mar. 14, 2018 for U.S. Appl. No. 15/202,785.
Office Action dated May 22, 2015 for U.S. Appl. No. 14/212,096.
Office Action dated Jun. 2, 2016 for U.S. Appl. No. 14/212,096.
Office Action dated Jun. 29, 2018 for U.S. Appl. No. 15/202,785.
Office Action dated Jul. 11, 2018 for U.S. Appl. No. 15/410,364.
Office Action dated Sep. 4, 2018 for U.S. Appl. No. 15/410,305.
Office Action dated Nov. 27, 2015 for U.S. Appl. No. 14/212,096.
European Search Report dated Mar. 6, 2019 for EP16821894.9.
Notice of Allowance dated Jun. 10, 2019 for U.S. Appl. No. 15/202,785.
Office Action dated Jan. 25, 2019 for U.S. Appl. No. 15/202,785.
Office Action dated Feb. 8, 2019 for U.S. Appl. No. 15/410,305.
European Search Report dated Aug. 26, 2019 for EP17741885.2.
Office Action dated Jul. 9, 2019 for U.S. Appl. No. 15/410,305.
International Search Report and Written Opinion dated Apr. 2, 2019 for PCT/US2018/060089.
Notice of Allowance dated Feb. 14, 2020 for U.S. Appl. No. 15/410,305.
European Search Report dated Jul. 9, 2021 for EP18876110.0.

* cited by examiner

STAGED DEFLATION SYRINGE SYSTEMS AND ASSOCIATED METHODS

RELATED APPLICATIONS

This application claims priority to U.S. Provisional Application No. 62/585,234, filed on Nov. 13, 2017 and titled, "Staged Deflation Syringe Systems and Associated Methods," which is hereby incorporated by reference in its entirety.

TECHNICAL FIELD

The present disclosure relates to medical instruments and systems for providing hemostasis at a vascular puncture site. The features relating to the methods and devices described herein can be applied to any hemostasis device utilizing a syringe to deflate the hemostasis device by stages.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

DETAILED DESCRIPTION

Figure 1:
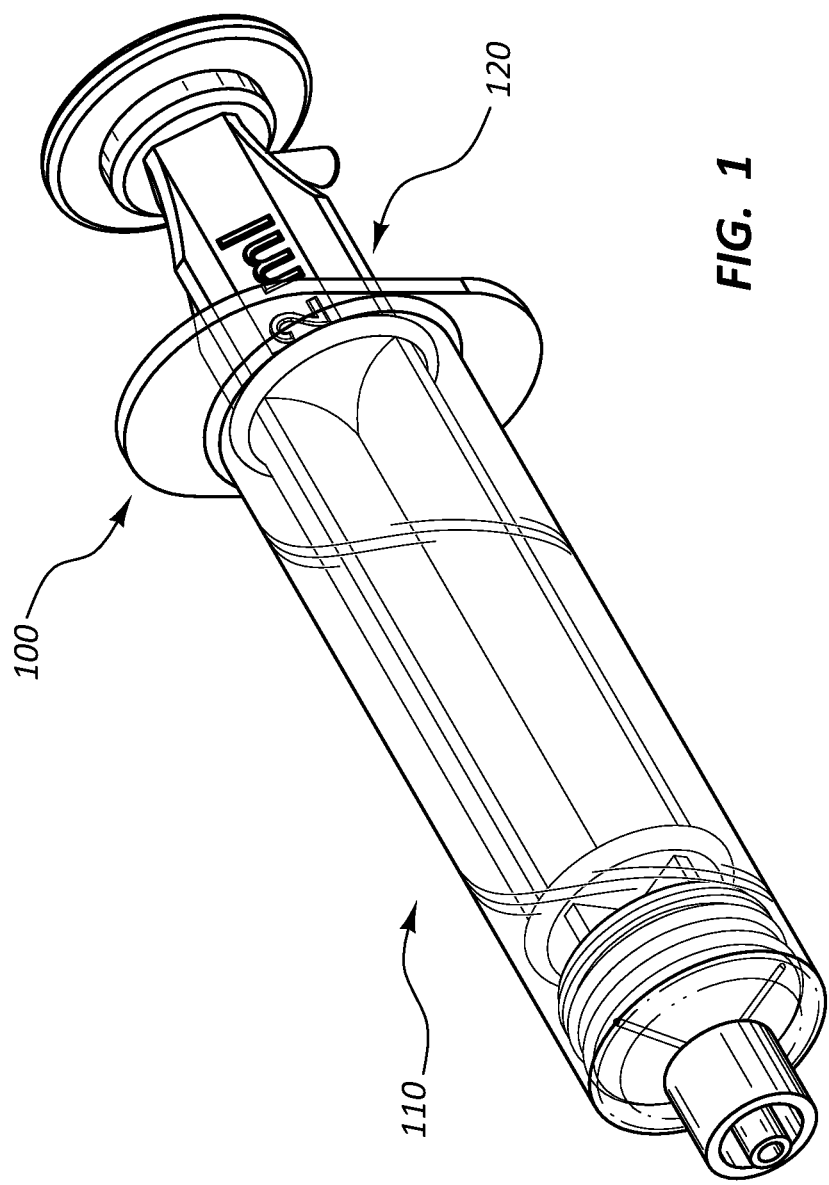
FIG. 1 is a perspective view of a staged deflation syringe.

Medical procedures which include access to a patient's cardiovascular system are commonly performed in hospitals and outpatient clinics. Such procedures may be performed to diagnose or provide therapeutic treatment for a medical issue. Access to the cardiovascular system may entail the use of needles, guidewires, and long catheters. Upon removal of these devices, a puncture hole remains open in a wall of a vessel. Blood may leak from the puncture hole resulting in a hematoma or blood loss. Due to a higher pressure within arteries, the risk of hematoma or blood loss is higher when an artery is accessed for a procedure. In some procedures, the puncture hole is occluded with a device to plug the hole or pressure is applied over the puncture hole following removal of an access device until the hole is occluded by a blood clot. Pressure may be applied in a variety of ways, including by hand, a sandbag, a pressure dressing, or by an inflatable hemostasis device.

Some inflatable hemostasis devices may be deflated in stages over time. A syringe may be utilized to deflate the inflatable hemostasis device. Achievement of timely hemostasis may avoid complications, facilitate patient discharge, and quick turnover of the procedure room.

Embodiments of the disclosure may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to, or in communication with, each other even though they are not in direct contact with each other. For example, two components may be coupled to, or in communication with, each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to a deflation syringe, the proximal end of the syringe refers to the end nearest the flange and the distal end refers to the opposite end, the end nearest the inlet/outlet port of the syringe.

FIGS. 1-4B illustrate different views of a staged deflation syringe and related components. In certain views each syringe may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any figure or embodiment.

FIGS. 1-4B depict an embodiment of a staged deflation syringe 100. In the illustrated embodiment, the staged deflation syringe 100 comprises a barrel member 110 and a plunger member 120, in addition to other components.

Figure 2A:
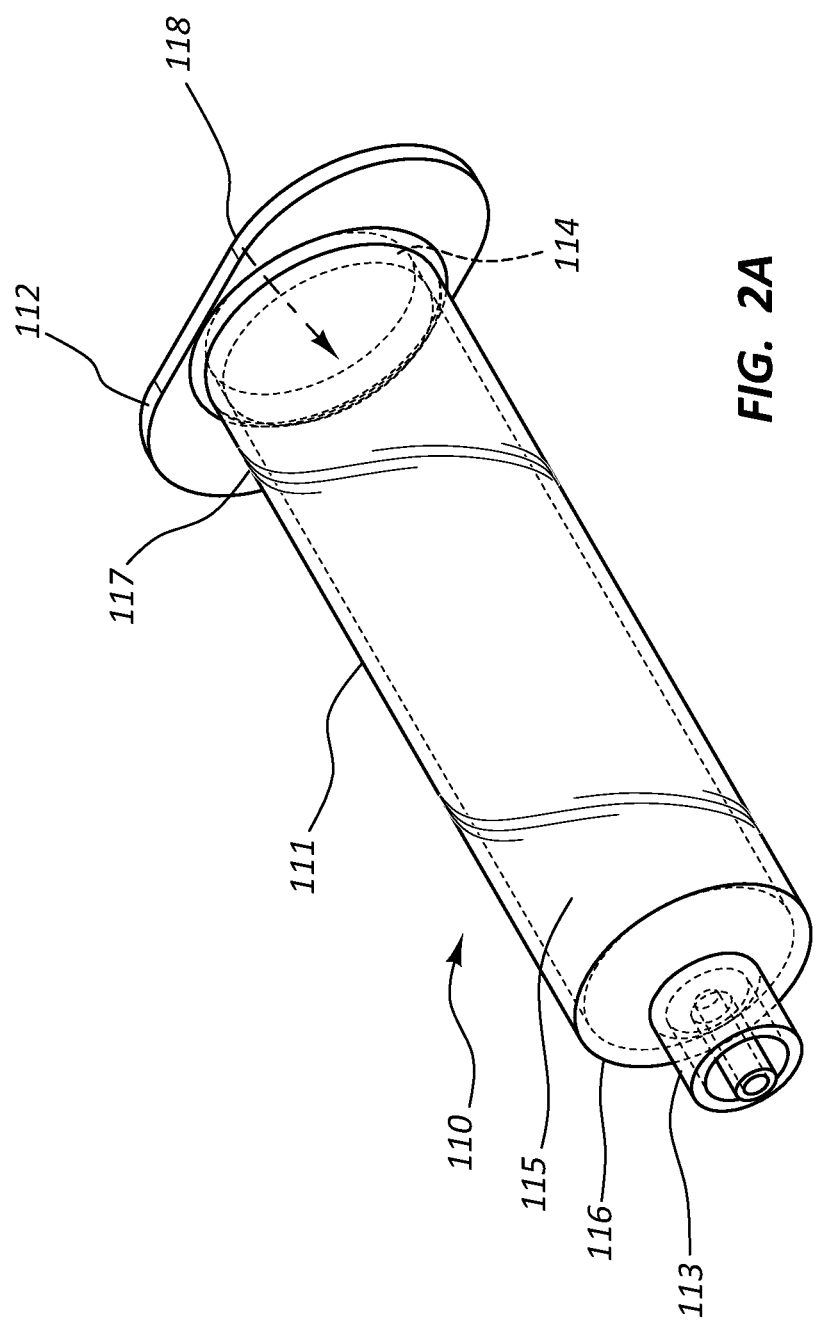
FIG. 2A is a perspective view of a syringe barrel member of the staged deflation syringe of FIG. 1.
Figure 2B:
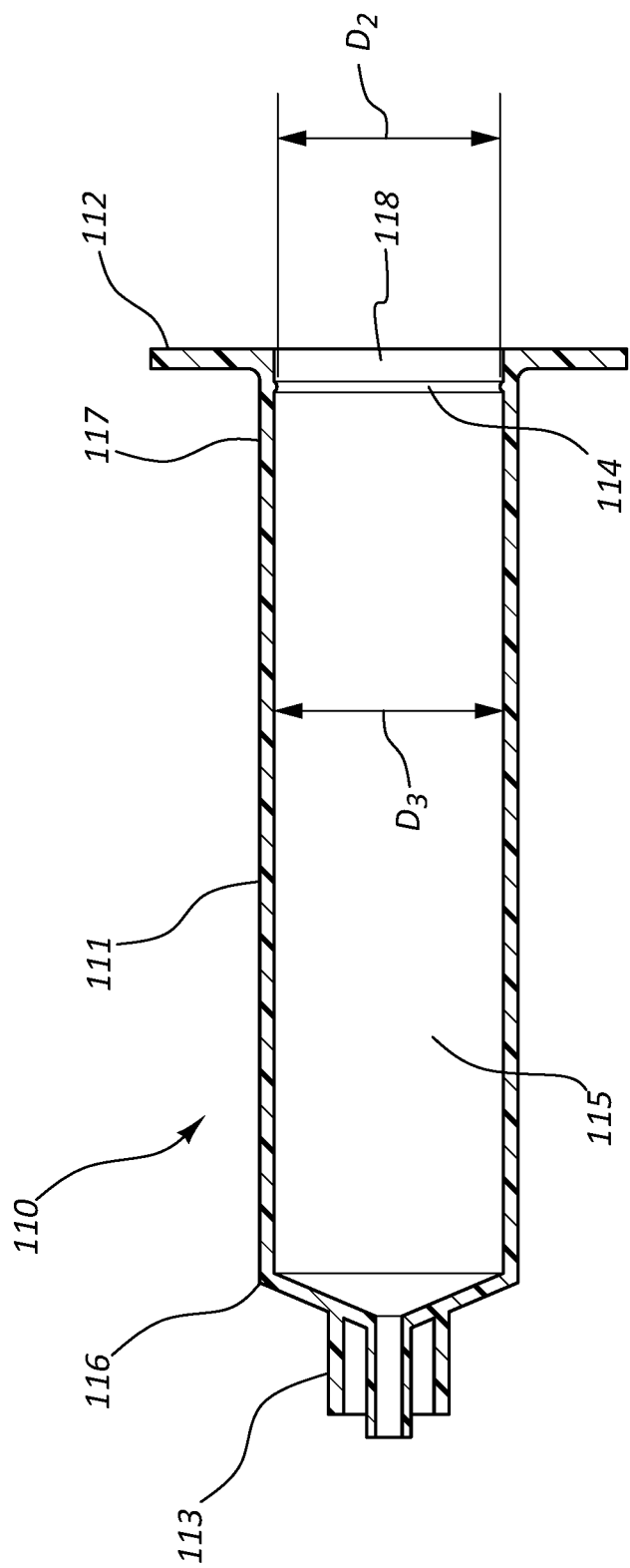
FIG. 2B is a cross-section view of the syringe barrel member of FIG. 2A.

FIG. 2A is a perspective view of the barrel member 110 of the staged deflation syringe 100 and FIG. 2B is a cross-section view of the barrel member 110. The barrel member 110 of the illustrated embodiment comprises a barrel 111, a flange 112, and a port 113. The barrel 111 may be cylindrical in shape with a bore 115 which defines a reservoir for air or liquids. Other barrel 111 shapes are within the scope of this disclosure. The barrel 111 further comprises a proximal opening 118 disposed adjacent to a proximal end portion 117. Indices may be disposed on an outer surface of the barrel 111. The indices may indicate the volume of the bore 115 in increments of milliliters, tenths of milliliters, hundredths of milliliters or any other suitable volume measurement. The indices may be applied to the barrel 111 using any suitable technique, such as, transfer printing, laser printing, adhesive labels, etc. The barrel member 110 may be formed from any suitable rigid or semi-rigid polymeric material, such as polycarbonate, polypropylene, polyethylene, etc. The barrel member 110 may be manufactured using any suitable manufacturing technique, such as injection molding, casting, machining, etc.

The barrel member 110 further comprises a retention ring 114 disposed adjacent the proximal end portion 117 of the barrel 111. The retention ring 114 extends radially inwardly from a wall of the bore 115. The retention ring 114 may be configured to extend circumferentially without breaks, or it may be segmented into two or more portions. The retention ring 114 may have a height of 0.01 inch to 0.10 inch, including 0.04 inch to 0.06 inch. The retention ring 114 may be shaped in any suitable shape, such as the shape of a semi-circle, the shape of a right triangle where the vertical leg is oriented distally and the inclined leg is oriented proximally, etc. Functions of the retention ring 114 are further detailed below.

The flange 112 of the barrel member 110 is disposed adjacent the proximal end portion 117. The flange 112 is configured to provide finger gripping surfaces. The flange 112, in the depicted embodiment, comprises two portions which extend radially outward from a central axis of the barrel 111. In some embodiments, the flange 112 may comprise a circular shape such that the flange 112 extends circumferentially radially outward from the central axis of the barrel 111. The flange 112 may further comprise any suitable grip enhancing feature, such as ribs, dimples, detents, grooves, etc.

The port 113 is disposed adjacent a distal end portion 116 of the barrel 111. In the illustrated embodiment, the port 113 is configured as a male Luer fitting having a Luer taper outer surface and a lumen that is in fluid communication with the bore 115 of the barrel 111. In other embodiments, the port 113 may be configured as a male Luer lock fitting having an internally threaded collar configured to couple with external threads of a female Luer lock connector. Still further various port 113 shapes, fittings, and connectors are within the scope of this disclosure.

Figure 3:
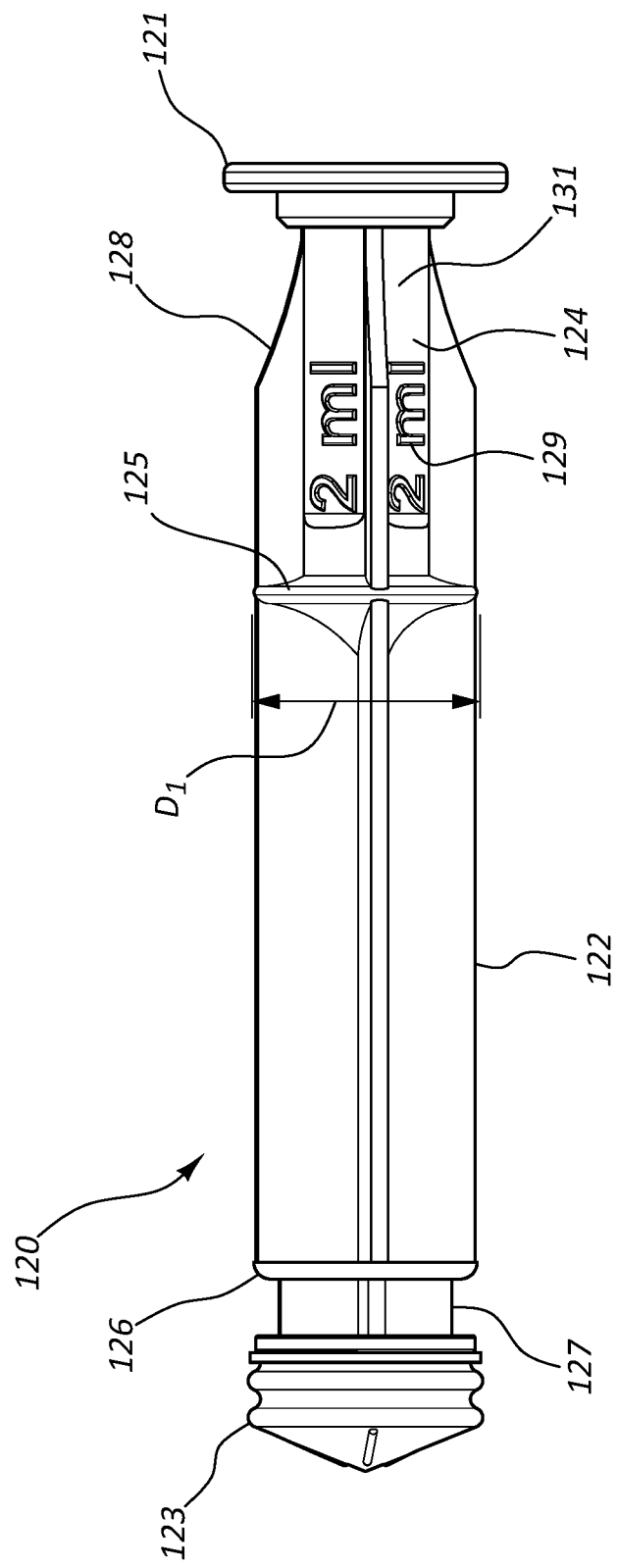
FIG. 3 is a side view of a syringe plunger member of the staged deflation syringe of FIG. 1.

Referring to FIG. 3, a side view of the plunger member 120 is shown. The plunger member 120 is configured to be, at least partly, longitudinally disposed within the bore (115 of FIGS. 2A and 2B) of the barrel (111 of FIGS. 2A and 2B). In the illustrated embodiment, the plunger member 120 comprises a body 126, a plunger tip 123, and an insert 124. The body 126 comprises longitudinally oriented ribs 122. The ribs 122 may comprise any suitable number, such as two, three, four, etc. In some embodiments, the body 126 comprises a longitudinally extending cylindrical shaft. A plunger flange 121 is disposed adjacent a proximal end portion 128 of the body 126. The plunger flange 121 is configured to facilitate axial displacement of the plunger member 120 by a healthcare worker. The plunger flange 121 may be shaped as a circular disk or any other suitable shape. The plunger flange 121 may be oriented perpendicular to a longitudinal axis of the body 126. The plunger flange 121 may comprise grip enhancing features on a proximal surface. The grip enhancing features may comprise ridges, grooves, dimples, detents, surface texturing, etc. The body 126 may be formed from any suitable rigid or semi-rigid polymeric material, such as polycarbonate, polypropylene, polyethylene, ABS, etc. The body 126 may be manufactured using any suitable technique, such as injection molding, casting, machining, etc.

With continued reference to FIG. 3 as well as FIGS. 2A and 2B, a distal end portion 127 of the body 126 may be configured to be coupled to the plunger tip 123. The plunger tip 123 is configured to seal against a wall of the bore 115 of the barrel 111 such that negative or positive pressures are generated within the bore 115 distal to the plunger tip 123 when the plunger member 120 is displaced axially along the bore 115 of the barrel 111. The plunger tip 123 may be formed of any suitable elastomeric material, such as rubber, thermoplastic elastomers, etc. The plunger tip 123 may be manufactured using any suitable technique for elastomeric materials, such as injection molding, transfer molding, compression molding, etc.

The insert 124 may be coupled to the body 126 and disposed adjacent the proximal end portion 128 of the body 126. In some embodiments, the insert 124 may be integrally formed with the body 126, including embodiments wherein the insert 124, or any portion thereof (such as the insert flange 125 discussed below) is a molded feature of the plunger body 126. In the embodiment of FIGS. 1-4B, the insert 124 is configured to engage with the retention ring 114 when the plunger member 120 is proximally displaced or retracted, such that interference between the retention ring 114 and the insert 124 restricts retraction of the plunger member 120 with respect to the barrel member 111.

In the illustrated embodiment, the insert 124 comprises an insert flange 125 and an extension portion 131. The insert 124 may be formed from any suitable rigid polymeric or semi-rigid material, such as polycarbonate, polypropylene, polyethylene, ABS, etc. The insert 124 may be coupled to the body 126 using any suitable technique, such as overmolding, heat welding, sonic welding, adhesive, etc.

The insert flange 125 extends radially outward from the longitudinal axis of the body 126. The insert flange 125 may be disposed between the ribs 122 of the body 126. In some embodiments, the insert 124 is disposed between at least two ribs 122 such that the insert flange 125 forms an arc between the two ribs 122. In other embodiments, the insert 124 is disposed between more than two ribs 122 such that the insert flange 125 forms a circumferential arc around the body 126.

Figure 4A:
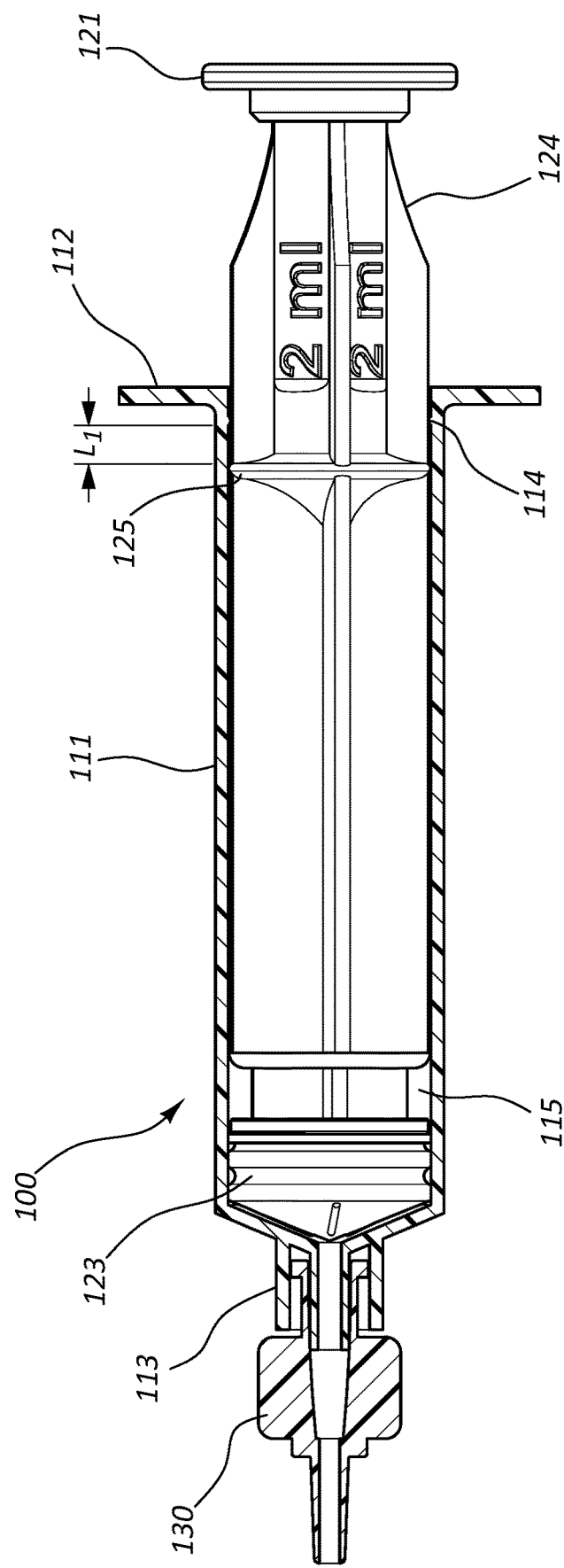
FIG. 4A is a side view of the staged deflation syringe of FIG. 1 and a connector, with the barrel and connector shown in cross-section to illustrate internal components, with the staged deflation syringe in a ready configuration.

In the illustrated embodiment, the outside diameter $D_1$ of the insert flange 125 is configured to be greater than inside diameter $D_2$ (FIG. 2B) of the retention ring 114 of the barrel 111 and less than the inside diameter $D_3$ (FIG. 2B) of the bore 115 such that the plunger member 120 is slidably displaceable within the bore 115 within a restricted stroke distance $L_1$ (FIG. 4A). The outer edge of the insert flange 125 may be radiused or squared or have any other suitable shape configured to engage with the retention ring 114. For example, in some embodiments, the outer edge of the insert flange 125 may be formed in the shape of a right triangle where the vertical leg is oriented proximally and the inclined leg is oriented distally such that insert flange 125 is configured to couple with a mating shape of the retention ring 114.

In some embodiments, the insert flange 125 and/or the retention ring 114 may be deformed when the insert flange 125 engages the retention ring 114 with adequate force such that the insert flange 125 may be retracted proximally to the retention ring 114. In other embodiments, the retention ring 114 may form a hard stop such that the insert flange 125 cannot be retracted proximally to the retention ring 114.

In still other embodiments, the retention ring 114 may be formed in an incomplete ring such that a gap is formed between ends of the retention ring 114. A diameter of the bore 115 between the ends of the retention ring 114 may be equivalent to the inside diameter D3 of the bore 115. The insert flange 125 may be configured as with arc segments configured to align with the gaps of the retention ring 114 such that the insert flange may be retracted proximally to the retention ring when the arc segments are aligned with the gaps.

In certain embodiments, the insert flange 125 may be positioned along the longitudinal axis of the barrel 111 such that the stroke distance $L_1$ of the plunger member 120 is restricted to provide a desired volume of air or liquid within a portion of the bore 115. For example, the insert flange 125 may be positioned along the body 126 such that 1 milliliter, 2 milliliter, 3 milliliter, 4 milliliter, or any other desired volume of air or liquid may be drawn into the portion of the bore 115 distal to the plunger tip 123. In some embodiments, the insert flange 125 may be fixedly coupled to the body 126 at the desired position to provide the desired volume of air or liquid. In other embodiments, the insert 124 may be longitudinally adjustable such that the insert flange 125 can be positioned at a variety of desired locations along the body 126 by the healthcare worker at the time of use. The insert 124 and the body 126 may comprise a ratchet mechanism to facilitate adjustability of the position of the insert flange 125. Further, embodiments wherein the retention ring 114 and/or insert flange 125 are disposed other portions of the barrel 111 are within the scope of this disclosure.

In the illustrated embodiment, the extension portion 131 of the insert 124 is shown to extend longitudinally toward the proximal end portion 128 of the body 126. The extension portion 131 may be disposed between at least two ribs 122. In other embodiments, the extension portion 131 may be disposed between 3, 4, 5, or any number of ribs 122. The extension portion 131 may comprise an indicia to indicate the volume of air or liquid the staged deflation syringe 100 is configured to withdraw from an inflatable hemostasis device.

Figure 4B:
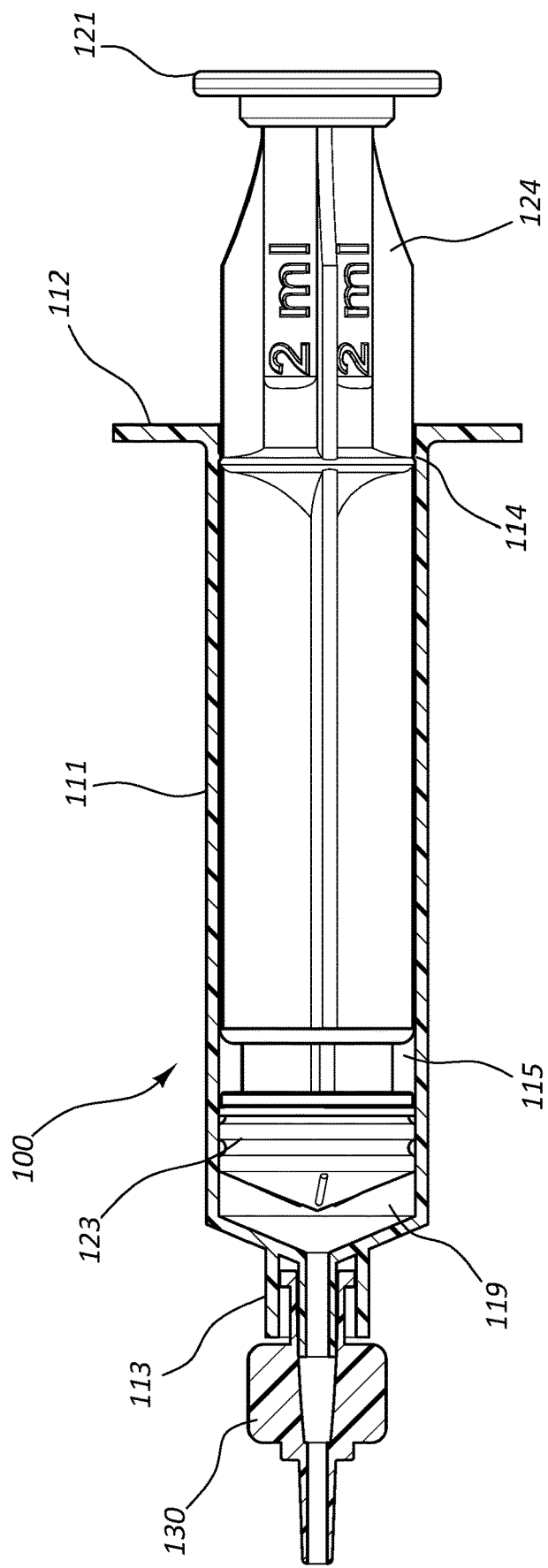
FIG. 4B is a side view of the staged deflation syringe and connector of FIG. 4A, with the barrel and connector shown in cross-section to illustrate internal components, with the staged deflation syringe in a deflation configuration.

FIGS. 4A and 4B illustrate the staged deflation syringe 100 and a connector 130 in a ready configuration and retracted configuration, respectively. In FIGS. 4A and 4B the syringe barrel 111 and connector 130 are shown in cross-section to illustrate internal components. In use, the healthcare worker may partially deflate an inflatable hemostasis device by removing a small volume of air or fluid from the inflatable hemostasis device. The volume of air or fluid to be removed may be 1 milliliter, 2 milliliter, 3 milliliter, 4 milliliter, or any other volume up to the volume of the inflatable hemostasis device. The healthcare worker may obtain the staged deflation syringe 100 in the ready configuration and couple the staged deflation syringe 100 to the inflatable hemostasis device (not shown).

The port 113 of the barrel 111 may be sealingly coupled to a connector 130 of the inflatable hemostasis device. The connector 130 may comprise a valve configured to retain the air or fluid within the inflatable hemostasis device under pressure until the connector is coupled to a device, such as the staged deflation syringe 100. Upon coupling, pressure within the inflatable hemostasis device may be adequate to cause the air or liquid within the inflatable hemostasis device to flow from the inflatable hemostasis device through the connector 130, through the port 113, and into the bore 115 as the plunger member 120 is driven proximally to the retracted configuration. The plunger member 120 is driven proximally until the insert flange 125 couples with the retention ring 114. An excess of air or fluid cannot flow into a distal portion 119 of the bore 115 due to restriction of distal axial movement of the plunger member 120 such that the inflatable hemostasis device is deflated a desired volume. Excess deflation of the inflatable hemostasis device may result in bleeding from or hematoma formation at the vascular puncture site due to a reduced applied pressure at the puncture site. The deflation process may be repeated over time until the inflatable hemostasis device is fully deflated and hemostasis of the puncture site is achieved. For example, the staged deflation syringe 100 may be decoupled from the connector 130 for a period of time, such as 15 minutes. The staged deflation syringe 100 may then be recoupled to the connector 130 with the plunger member 120 distally positioned.

In some embodiments, the pressure within the inflatable hemostasis device is not high enough to drive the plunger member 120 distally even when the valve of the connector 130 is opened by the staged deflation syringe 100. In such instances, the healthcare worker may grasp the plunger flange 121 with fingers and manually displace the plunger member 120 axially distally until the insert flange 125 engages with the retention ring 114. As the plunger member 120 is axially displaced, air or fluid is drawn into the distal portion 119 of the bore 115 by negative pressure created within the distal portion 119.

Without further elaboration, it is believed that one skilled in the art may use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A staged deflation syringe device, comprising:
a barrel member comprising a retention ring; and
a plunger member disposed at least partly within the barrel member;
an insert member with a plurality of longitudinal ribs coupled to the plunder member, the insert member includes a flange configured to engage with the retention ring of the barrel member to restrict retraction of the plunger member,
wherein the insert member further comprises at least one extension member, each of the at least one extension members is disposed between two of the plurality of longitudinal ribs, extends in a proximal to distal direction, and is disposed on a different plane than the two longitudinal ribs, and
wherein at least one of the insert member and the retention ring are configured to deform when adequate force is applied such that the insert member is retractable proximal to the retention ring.

2. The staged deflation syringe device of claim 1, wherein the retention ring is spaced from a proximal end of the barrel member.

3. The staged deflation syringe device of claim 2, wherein the flange comprises one or more arc segments in the circumferential direction of the plunger.

4. The staged deflation syringe device of claim 1, wherein the plunger member is retractable in an increment that is less than the full volume of the barrel member.

5. The staged deflation syringe device of claim 4, further comprising indicia on the at least one extension member of the insert member that corresponds to the volume of air or liquid the staged deflation syringe device withdraws when the flange engages with the retention ring.

6. The staged deflation syringe device of claim 1, wherein the insert member comprises a ratchet mechanism and the plunger member comprises a plunger body with a mating ratchet mechanism, wherein the insert member is configured to be adjustable to multiple positions.

7. The staged deflation syringe device of claim 6, wherein the insert member is configured to restrict retraction of the plunger member to one or more distances.

8. The staged deflation syringe device of claim 1, wherein a cross section of the retention ring is in the shape of a semi-circle or a right triangle.

9. The staged deflation syringe device of claim 1, wherein the flange has an outer edge that is radiused or squared.

10. The staged deflation syringe device of claim 1, wherein the plunger member is a fixed overall length.

\* \* \* \* \*